United States Patent [19]
Schulz et al.

[11] Patent Number: 6,090,956
[45] Date of Patent: Jul. 18, 2000

[54] PREPARATION OF EPOXIDES FROM OLEFINS USING BIS(TRIORGANOSILYL) PEROXIDES IN THE PRESENCE OF ACTIVATORS BASED ON METALLIC ACID DERIVATIVES

[75] Inventors: Michael Schulz; Joaquim Henrique Teles, both of Ludwigshafen; Jörg Sundermeyer, Marburg-Michelbach; Günter Wahl, Würzburg, all of Germany

[73] Assignee: BASF Aktiengesellschaft, Ludwigshafen, Germany

[21] Appl. No.: 09/142,042

[22] PCT Filed: Feb. 28, 1997

[86] PCT No.: PCT/EP97/00982

§ 371 Date: Sep. 2, 1998

§ 102(e) Date: Sep. 2, 1998

[87] PCT Pub. No.: WO97/32867

PCT Pub. Date: Sep. 12, 1997

[30] Foreign Application Priority Data

Mar. 4, 1996 [DE] Germany ............... 19608004

[51] Int. Cl.$^7$ .............. C07D 301/19; C07D 301/12
[52] U.S. Cl. ............................ 549/529; 502/174
[58] Field of Search ................ 549/529; 502/174

[56] References Cited

U.S. PATENT DOCUMENTS 3,953,362 4/1976 Lines et al. ............... 252/431 W

FOREIGN PATENT DOCUMENTS 0 097 551 1/1984 European Pat. Off. .
2 489 710 3/1982 France .
WO 97 10054 3/1997 WIPO .

OTHER PUBLICATIONS

Synthesis Communication, cf. Taddei and Ricci in Synthesis 1986, 633–635.
Pergamon Press Ltd., Matsubara et al. In Tetrahedron Lett. 1983, vol. 24, pp. 3741–3744.
The Chemical Society of Japan, 58, 844–849 (1985) vol. 58, No. 3.
Synlett (Synles, 09365214); 1994; (4) pp. 255–256, Kyushu Univ.; Dep. Chem.; Fukuoka; 812; Japan, Irie et al: "Enantioselectives using hydrogen peroxide as a terminal oxidant".
Chemische Berichte, vol. 127, 1994, pp. 1201–1212, Sundermeyer et al "Homoscorpionate als tripodale . . . ".

*Primary Examiner*—Ba K. Trinh
*Attorney, Agent, or Firm*—Oblon, Spivak, McClelland, Maier & Neustadt, P.C.

[57] ABSTRACT

Epoxides are prepared from olefins using bis(triorganosilyl) peroxides in the presence of activators based on metalic acid derivatives of the formula $$[MO_XX_YL_Z]_n$$

where
- M is a metal of transition groups IV to VII, in particular molybdenum, tungsten or rhenium
- L is an uncharged ligand selected from the group consisting of amine oxides, phosphine oxides, arsine oxides, phosphoric triamides, formamides and pyridine N-oxides
- X is an inorganic ligand
- x is from 1 to 5
- y is 0, 1 or 2,
- Z is 1 or 2 and
- n is 1 or 2.

9 Claims, No Drawings

PREPARATION OF EPOXIDES FROM OLEFINS USING BIS(TRIORGANOSILYL) PEROXIDES IN THE PRESENCE OF ACTIVATORS BASED ON METALLIC ACID DERIVATIVES

This application is a 371 of PCT/EP97/00982 dated Feb. 28, 1997.

The present invention relates to an improved process for preparing epoxides from olefins using bis(triorganosilyl) peroxides in the presence of activators based on certain metallic acid derivatives.

While oxidants such as hydrogen peroxide HOOH or alkyl hydroperoxides ROOH have a firmly established place in organic synthesis, the synthetic potential of bis (triorganosilyl) peroxides (BTSPs), in particular the readily available bis(trimethylsilyl) peroxide ($TMS_2O_2$), is restricted to a few applications.

Thus, BTSPs have been used as sources of "$OH^+$" for the stoichiometric electrophilic hydroxylation of carbanions, for instance aryllithium compounds, vinyl anions, α-sulfonyl-carbanions and also lithiated carboxylic acids and their amides (cf. Taddei and Ricci in Synthesis 1986, 633). The Baeyer-Villiger oxidation of ketones by BTSPs and the electrophilic hydroxylation of electron-rich aromatics in the presence of noncatalytic amounts of Lewis acids such as $BF_3$, $AlCl_3$ or $SnCl_4$ are also known.

However, catalytic activation of BTSPs by metal complexes has hitherto only been successful in the case of the oxidation of primary and secondary alcohols to form aldehydes and ketones; the catalysts used here are pyridinium dichromate or the palladium complex $PdCl_2(PPh_3)_2$. In contrast, attempts at the metal-catalyzed activation of BTSPs for the epoxidation of olefins have remained unsuccessful. Thus, Matsubara et al. in Tetrahedron Lett. 1983, 24, 3741 and in Bull. Chem. Soc. Jpn. 1985, 58, 844 reported unsuccessful attempts to activate $TMS_2O_2$ by means of the acetylacetonates $VO(acac)_2$ and $MoO_2(acac)_2$. Instead of the hoped-for epoxidation of the allyl alcohols used, only isomerization of the olefinic double bond was observed.

It is an object of the present invention to provide an effective activator for the epoxidation of olefins using BTSPs.

We have found that this object is achieved by a process for preparing epoxides of the formula

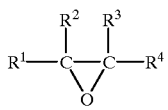

where $R^1$ to $R^4$ are identical or different and are hydrogen or substituted or unsubstituted alkyl, alkenyl, heteroalkyl, cycloalkyl, aryl or heteroaryl radicals, or the radicals $R^1$ to $R^4$ can also be linked to one another to form rings or are is substituents based on elements of main groups IV to VII of the Periodic Table of the Elements, from olefins of the formula

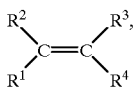

wherein bis(triorganosilyl) peroxides of the formula

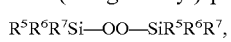

where $R^5$ to $R^7$ are hydrocarbon radicals which may be unsubstituted or substituted by functional groups, are used as epoxidizing agents in the presence of activators based on metallic acid derivatives of the formula

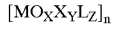

where

M is a metal of transition groups IV to VII of the Periodic Table of the Elements, L are uncharged ligands selected from the group consisting of amine oxides, phosphine oxides, arsine oxides, stibine oxides, phosphoric triamides, formamides and pyridine N-oxides, X are anionic ligands selected from the group consisting of halides, alkyl groups, alkoxy groups, aryloxy groups, trialkylsilyl groups, hydroxyl groups, metallic anhydride groups of the formula —$OMO_x$, carboxylic ester groups, sulfonic ester groups, phosphonic ester groups, carbonic ester groups, sulfuric ester groups, phosphoric ester groups, hydroperoxy groups, peroxy-alkyl groups and triorganosilylperoxy groups, where two variables X can also represent a peroxo function, x is an integer from 1 to 5, y is 0, 1 or 2, Z is 1 or 2 and n is 1 or 2, where two uncharged ligands L, two anionic ligands X or one uncharged ligand L and one anionic ligand X may be linked to a chelating ligand either directly or via an alkylene bridge.

A prerequisite for a catalytically active activator for the purposes of the present invention is the ability of its oxo ligands [M=O] to react with the silyl peroxides of the $R^5R^6R^7Si$—OO—$SiR^5R^6R^7$ type so as to convert them into a metal(silylperoxy) function [$M(O_2$—$SiR^5R^6R^7)$] or a metal(peroxo) function [$M(\eta^2$—$O_2)$], the latter with liberation of the corresponding siloxane $R^5R^6R^7Si$—O—$SiR^5R^6R^7$. The decisive question for catalysis is whether silyl groups can, similarly to protons, migrate within the O-ligand regime in oxo(peroxo) complexes.

For this reason, latently coordinately unsaturated metal-oxo and -peroxo complexes which meet this criterion of rapid silyl group migration are central to the present invention as activators for the epoxidation system described. The metallic acid derivatives mentioned above are such compounds.

Possible metals M in the metallic acid derivatives mentioned are, in particular, titanium, zirconium, hafnium, vanadium, niobium, tantalum, chromium, manganese and in particular molybdenum, tungsten and rhenium. In a preferred embodiment, activators used are metallic acid derivatives in which M is molybdenum or tungsten and at the same time n is 1 or in which M is rhenium and n is 1 or 2. Examples of such species are the activator structures Ib, IIb, IIIb and IVb shown further below.

Suitable uncharged ligands L are, in particular, amine oxide or phosphine oxide ligands of the formulae

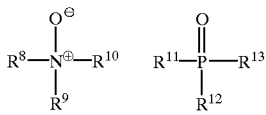

where
R$^8$ to R$^{10}$ and R$^{11}$ to R$^{13}$ are identical or different C$_1$–C$_{30}$-alkyl, C$_7$–C$_{30}$-aralkyl or C$_6$–C$_{30}$-aryl or hetaryl radicals which may additionally contain ether oxygen atoms, carbonyl groups, hydroxyl groups, alkoxy groups, carboxyl groups, cyano groups, carboxylic ester groups, sulfo groups, phosphonic acid groups, nitro groups, halogen atoms and/or unsubstituted or C$_1$–C$_4$-alkyl-substituted amino groups as functional groups.

Typical examples of such amine N-oxide ligands are:
dimethyl-n-undecylamine oxide,
dimethyl-n-dodecylamine oxide,
dimethyl-n-tetradecylamine oxide,
dimethyl-n-hexadecylamine oxide,
dimethyl-n-octadecylamine oxide,
dimethyl-n-eicosylamine oxide,
methyl-di(n-dodecyl)amine oxide,
methyl-di(n-octadecyl)amine oxide,
tri(n-butyl)amine oxide,
tri(n-hexyl)amine oxide,
tri(n-octyl)amine oxide,
tri(2-ethylhexyl)amine oxide,
tri(n-dodecyl)amine oxide,
tri(n-octadecyl)amine oxide,
benzyl-di(n-dodecyl)amine oxide,
diphenyl-n-octadecylamine oxide,
N-undecylmorpholine oxide,
N-dodecylpiperidine oxide,
dimethyl-(6-phenylhexyl)amine oxide,
dimethyl-bisphenylamine oxide and
methyl-n-dodecyl-(6-phenylhexyl)amine oxide.

Typical examples of such phosphine oxide ligands are:
tri-n-butylphosphine oxide,
tri-tert-butylphosphine oxide,
tri-n-pentylphosphine oxide
tri-n-hexylphosphine oxide,
tri-n-octylphosphine oxide,
tri-(2-ethylhexyl)phosphine oxide,
tri-n-dodecylphosphine oxide,
tri-n-octadecylphosphine oxide,
di-n-butyl-n-octylphosphine oxide,
n-butyl-di-n-octylphosphine oxide,
tribenzylphosphine oxide,
benzyl-di-n-octylphosphine oxide,
naphthyl-di-n-octylphosphine oxide and
di-n-butyl-naphthylphosphine oxide.

If the radicals R$^8$ to R$^{10}$ and R$^{11}$ to R$^{13}$ contain additional ether oxygen atoms, such radicals are derived, in particular, from corresponding ethylene oxide, propylene oxide or butylene oxide reaction products or from tetrahydrofuran reaction products.

Alkoxy substituents and carboxylic ester substituents in R$^8$ to R$^{10}$ and R$^{11}$ to R$^{13}$ preferably have C$_1$–C$_4$-alkyl radicals, in particular methyl or ethyl. Halogen atoms are especially chlorine or bromine. If any of the functional groups listed are present in the radicals mentioned, the number present is usually from 1 to 3, in the case of ether oxygen atoms from 1 to 14 depending on chain length. Other ligands of particular interest are amine oxide and phosphine oxide ligands which contain carboxy methyl radicals, alkoxycarbonylmethyl radicals or 2-pyridyl radicals.

In addition, the following uncharged ligands L are also preferred:

arsine oxide ligands of the formula

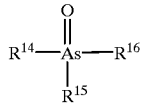

where the radicals R$^{14}$ to R$^{16}$ are as defined for R$^8$ to R$^{10}$ and R$^{11}$ to R$^{13}$;

stibine oxide ligands of the formula

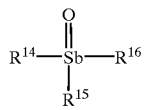

where the radicals R$^{14}$ to R$^{16}$ are as defined above;

phosphoric triamide ligands of the formula

(R$^{17}$R$^{18}$N)$_3$PO where R$^{17}$ and R$^{18}$ are hydrogen or identical or different C$_1$–C$_{30}$-alkyl, C$_7$–C$_{30}$-aralkyl or C$_6$–C$_{30}$-aryl or hetaryl radicals which may additionally contain ether oxygen atoms, carbonyl groups, hydroxyl groups, alkoxy groups, carboxyl groups, cyano groups, carboxylic ester groups, sulfo groups, phosphonic acid groups, nitro groups, halogen atoms and/or unsubstituted or C$_1$–C$_4$-alkyl-substituted amino groups as functional groups; a typical example of such a phosphoric triamide is hexamethylphosphoramide (HMPA);

formamide ligands of the formula

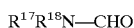

R$^{17}$R$^{18}$N—CHO where R$^{17}$ and R$^{18}$ are as defined above; typical examples of such formamides are N,N-dimethylformamide (DMF) and N-methyl-N-stearylformamide;

pyridine N-oxide ligands which are substituted in one or more ring positions, preferably in the 2 and/or 4 positions, by a C$_1$–C$_{30}$-alkyl, C$_7$–C$_{30}$-aralkyl or C$_6$–C$_{30}$-aryl or hetaryl radical which may additionally contain ether oxygen atoms, carbonyl groups, hydroxyl groups, alkoxy groups, carboxyl groups, cyano groups, carboxylic ester groups, sulfo groups, phosphonic acid groups, nitro groups, halogen atoms and/or unsubstituted or C$_1$–C$_4$-alkyl-substituted amino groups as functional groups or by a halogen atom such as fluorine, chlorine or bromine, a hydroxy group, a C$_1$–C$_{30}$-alkoxy radical or an unsubstituted or alkyl-substituted amino group; typical examples of such pyridine N-oxides are α- and γ-picoline N-oxide.

Typical examples of inorganic ligands X are:

fluoride and chloride (resulting in: metallic acid fluorides or chlorides)

methyl (resulting in: alkyl-metal oxides, e.g. methylrhenium oxide)

methoxy (resulting in: methyl esters of metallic acids)

phenoxy (resulting in: phenyl esters of metallic acids)

trimethylsilyloxy (resulting in: trimethylsilyl esters of metallic acids)

hydroxyl (resulting in: protic metallic acids)

$OMO_x$ (resulting in: metallic acid anhydrides, e.g. $Re_2O_7$ and $MoO_3$)

radicals of mixed metallic acid anhydrides such as acetates, sulfonates, phosphonates, organocarbonates, organosulfates and organophosphates which may be partially fluorinated or perfluorinated in their organic part

OOH $OOSi(CH_3)_3$

Activators used are preferably metallic acid derivatives in which, when y=1 or 2, X is chloride, fluoride, $C_1$–$C_4$-alkoxy, tri($C_1$–$C_4$-alkyl)silyl or metallic acid anhydride radicals of the formula $—OMoO_x$, $—OWO_x$ or $OReO_x$.

Examples of ligands L or X linked to a chelating ligand are 2,2'-bipyridyl N-oxide or N,N,N',N'-tetrabutylethylenediamine N,N'-oxide; in the latter case, the two ligands are linked by means of a $C_1$–$C_3$-alkylene bridge (here: 1,2-ethylene bridge).

The activators based on metallic acid derivatives of the formula $$[MO_XX_YL_Z]_n$$

are known in principle from the German Patent Application 195 33 331.4, in which they are described as activators for epoxidation using hydrogen peroxide. Similar metallic acid derivatives are described by Sundermeyer et al. in Chem. Ber. 1994, 127, 1201–1212.

Suitable bis(triorganosilyl) peroxides are, in particular, ones having the abovementioned formula in which $R^5$ to $R^7$ are as defined for $R^8$ to $R^{10}$ and $R^{11}$ to $R^{13}$. Particular preference is given to bis(tri-$C_1$–$C_4$-alkylsilyl) peroxides, very particular preference is given to bis(trimethylsilyl) peroxide.

The olefins which can be used are subject to no restriction in respect of the type and number of substituents. Typical examples of olefins which can be epoxidized by the process of the present invention are ethylene, propene, 1-butene, 2-butene, isobutene, 1,3-butadiene, 1-pentene, 2-pentene, isoprene, cyclopentene, 1-hexene, cyclohexene, $C_8$–$C_{24}$-α-monoolefins, styrene, indene, norbornene, cyclopentadiene, dicyclopentadiene and also alkene oligomers having reactive double bonds, e.g. polypropene and polyisobutene.

The olefins may also bear substituents based on elements of main groups IV to VII on the olefinic double bond. Examples are vinylsilicones, vinylamines, vinylphosphines, vinyl ethers, vinyl sulfides and halogenated alkenes such as vinyl chloride, vinylidene chloride or trichloroethylene.

The epoxidation process of the present invention is advantageously carried out by initially charging the olefin to be epoxidized together with the bis(triorganosilyl) peroxides and subsequently adding the activator based on metallic acid derivatives or a precursor thereof which is converted into the activator under the reaction conditions.

The bis(triorganosilyl) peroxide is normally mixed with the olefin to be epoxidized in a molar ratio of 1:1 (preferably with a slight excess of olefin). As a rule, no reaction is observed between these components, even over a prolonged time. The activator, for example Ib–IVb (see below), or else a soluble activator precursor, for example Ia–IVa (e.g. $MoO_2Cl_2$(dme), $WO_2Cl_2$(dme), $Re_2O_7$(dme) or $(CH_3)_3SiO—ReO_3$, dme=1,2-dimethoxyethane) and the ligand L are subsequently added thereto. The ligand L has the function of increasing the activity of the activator precursor, which in principle has some activity even in the absence of L, while simultaneously increasing the selectivity of the epoxidation reaction which proceeds rapidly after the addition of the activator.

Catalytically active compounds such as Ib–IVb can usually be isolated from the corresponding precursors such as Ia–IVa and characterized.

Activator Precursor

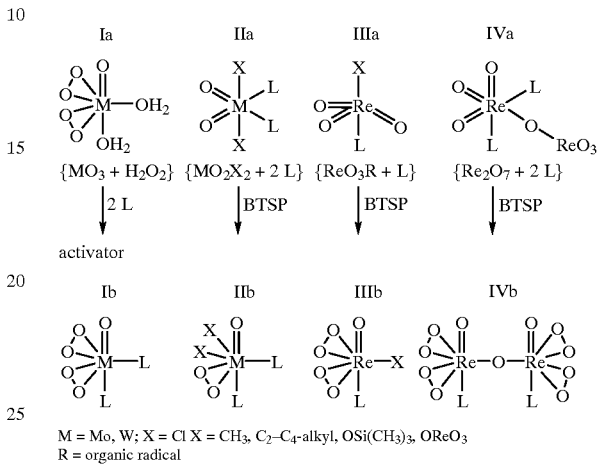

M = Mo, W; X = Cl X = $CH_3$, $C_2$–$C_4$-alkyl, $OSi(CH_3)_3$, $OReO_3$
R = organic radical Amine oxides, phosphine oxides, arsine oxides, stibine oxides and, somewhat more slowly, pyridine N-oxides as ligands L are here normally formed under the catalytic conditions from the corresponding tertiary amines, phosphines, arsines, stibines or pyridines and BTSP.

The epoxidation of the present invention is preferably carried out in an inert organic solvent at from 0 to 120° C., in particular from 10 to 100° C., especially from 20 to 80° C. It is generally carried out at atmospheric pressure. Suitable inert organic solvents are especially those selected from the group consisting of alkanes, aromatics, haloalkanes, haloaromatics, ethers, ketones, esters and tertiary alcohols (such as tert-butanol). The siloxane $R_3SiOSiR_3$, R=organic radical as defined, formed from the silyl peroxide during the reaction can also serve as such a solvent, so that it is not necessary to use any further solvent. When the radicals R are selected appropriately, the activator is homogeneously soluble in these media.

To make it easier to remove nonvolatile oxidation products, the activator described based on metallic acid derivatives can be used in bound form on an inorganic or organic support material which is insoluble in the reaction medium. Support materials which are suitable for this purpose are, in particular, those selected from the group consisting of silicon dioxide, silica gels, silicas, aluminum oxides, kaolins, aluminum silicates, poly-tert-amine N-oxides, polyvinylpyridine N-oxides and hexamethylphosphoramide chemically fixed on a polystyrene matrix.

Silica gels (silicic acid gels) are colloidal, shaped or unshaped silicas having an elastic to solid consistency, a loose to dense pore structure and a high adsorptive capability. Silica gel surfaces have acidic properties. Silica gels are usually prepared from water glass by reaction with mineral acids.

The silicas which can be used include not only the silicas prepared by wet methods but, particularly advantageously, also the finely divided "pyrogenic" $SiO_2$ grades obtained thermally, i.e. those customarily prepared by flame hydrolysis of $SiCl_4$ (e.g. Aerosils® or Sipernats®). In a preferred embodiment, use is made of silica having an average (agglomerate) particle size of from 100 nm to 30 μm, in particular from 1 μm to 20 μm, and an $SiO_2$ content of from 95 to 100% by weight, preferably from 98 to 100% by weight.

Aluminum oxides occur naturally as, for example, alumina or corundum. Here, the aluminum oxide is present in the α-modification. α-$Al_2O_3$ is obtained industrially from bauxite by the Bayer process. "Active" aluminum oxides having a high specific surface area which are particularly suitable as adsorbents are prepared from aluminum salt solutions by precipitation methods or from α-aluminum hydroxide by calcination.

Kaolins are hydrated aluminum silicates (clays) which occur naturally in the earth's crust and are also known as china clays because of their earlier main use in porcelain. Main constituents are the triclinic kaolinite and the monoclinic dickite and nacrite together with montmorillonite and gel-like aluminum silicates (allophanes).

Aluminum silicates are compounds which have different proportions of $Al_2O_3$ and $SiO_2$ and occur naturally as andalusite, sisthene, mullite, sillimanite, etc. Aluminum silicate minerals in which Al replaces Si as lattice sites in the crystal lattice are the aluminosilicates (e.g. ultramarines, zeolites, feldspars). Freshly precipitated aluminum silicates are finely divided and have a large surface area and a high adsorptive capability.

The present invention also provides the above-described activator complexes themselves, which are suitable in general for the catalytic activation of a series of chemical reactions, in particular oxidation reactions, especially for the catalytic epoxidation of olefins, and which comprise from 0.1 to 50% by weight, in particular from 0.5 to 30% by weight, of one or more catalytically active metallic acid derivatives of the formula $$[MO_XX_YL_Z]_n$$

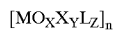

where
  M is a metal of transition groups IV to VII of the Periodic Table of the Elements,
  L are uncharged ligands selected from the group consisting of amine oxides, phosphine oxides, arsine oxides, phosphoric triamides, formamides and pyridine N-oxides,
  X are anionic ligands selected from the group consisting of halides, alkyl groups, alkoxy groups, aryloxy groups, trialkylsilyl groups, hydroxyl groups, metallic acid anhydride groups of the formula —$OMO_x$, carboxylic ester groups, sulfonic ester groups, phosphonic ester groups, carbonic ester groups, sulfuric ester groups, phosphoric ester groups, hydroperoxy groups, peroxyalkyl groups and triorganosilylperoxy groups, where two variables X can also represent a peroxo function,
  x is an integer from 1 to 5,
  y is 0, 1 or 2,
  z is 1 or 2 and
  n is 1 or 2,
    where two uncharged ligands L, two anionic ligands X or one uncharged ligand L and one anionic ligand x may be linked to a chelating ligand either directly or via an alkylene bridge, and
    from 50 to 99.9% by weight, in particular from 70 to 99.5% by weight, of one or more inorganic or organic support materials which are insoluble in the reaction medium and are selected from the group consisting of silicon dioxide, silica gels, silicas, aluminum oxides, kaolins, aluminum silicates, poly-tert-amine N-oxides, polyvinylpyridine N-oxides and hexamethylphosphoramide chemically fixed on a polystyrene matrix.

The epoxidation process of the present invention has a whole series of particular advantages. using bis (trimethylsilyl) peroxide ($TMS_2O_2$) as an example, these are discussed below in comparison with customary hydroperoxides or hydrogen peroxide:

$TMS_2O_2$ and other BTSPs are comparatively unproblematical peroxides in terms of handling and meet the highest demands on plant, warehouse and laboratory safety. Thus, $TMS_2O_2$ decomposes only above 200° C. and in a controlled manner. $TMS_2O_2$ and other BTSPs are activated only on addition of the specific catalyst, namely the above-described activators based on metallic acid derivatives, which promotes the heterolytic O—O dissociation. This class of substances does not have any particular tendency to decompose autocatalytically (free-radically), initiated by, for example, traces of heavy metals.

$TMS_2O_2$ can be prepared in relatively large quantities from largely recyclable raw materials (e.g. urea, TMSCl, $H_2O_2$, base) and can be safely stored for a virtually unlimited time.

Bis(triorganosilyl) peroxides are aprotic substitutes for anhydrous 100% strength $H_2O_2$. In the presence of a catalyst, these display a comparable oxidative strength, but the oxidation reactions generally proceed more selectively than when using $H_2O_2$.

As aprotic oxidants, bis(triorganosilyl) peroxides can also be used for the oxidation of hydrolysis-sensitive olefins (e.g. enolates, unsaturated carboxylic acid chlorides etc.).

The siloxanes $R_3SiOSiR_3$ formed in the redox reaction of bis(triorganosilyl) peroxides are barely basic, sterically bulky, i.e., poor ligands which have only a low coordination capability. A competitive reaction inhibition of the Lewis-acid metal center, known in the case of $H_2O$ or tert-BuOH (the reduction products of $H_2O_2$ or tert-BuOOH), is thus virtually ruled out.

Ring opening of the synthetically valuable epoxides to form synthetically less versatile diols (or their O-silyl ethers) as undesired subsequent reaction is effectively prevented by the low reactivity of the siloxanes. The latter problem always occurs in protic systems, for instance in the catalytic system $Re(O)(O_2)_2(CH_3)$ $(H_2O)/H_2O_2$/tert-BuOH/olefin.

Volatile epoxides can be separated from the reaction mixture particularly easily by means of distillation. In the case of less volatile products, the use of supported, i.e. immobilized, activator complexes (as described above), is possible.

In place of the pure bis(triorganosilyl) peroxides, it is also possible to use mixtures of the silyl peroxides and siloxanes for oxidation purposes. If the proportion of the siloxanes is appropriately high, these can also take over the role of the solvent.

EXAMPLES

A General Procedures for Preparing the Stock Solutions

Stock solution I: Olefin+oxidant+internal GC standard
Stock solution II: Metal complex or catalyst precursor
Stock solution III: Ligand

| Stock solution I | | (TMS)$_2$O$_2$ | $^n$Bu$_2$O (internal standard) |
|---|---|---|---|
| Cyclooctene | | | |
| Amount | 1.980 g (18.0 mmol) | 3.211 g (18.0 mmol) | 1.000 g (7.68 mmol) |
| | made up to 10.00 ml with CHCl$_3$ | | |
| Cyclopentene | | | |
| Amount | 1.230 g (18.0 mmol) | 3.211 g (18.0 mmol) | 1.000 g (7.68 mmol) |
| | made up to 10.00 ml with CHCl$_3$ | | |
| Norbornene | | | |
| Amount | 1.695 g (18.0 mmol) | 3.211 g (18.0 mmol) | 1.000 g (7.68 mmol) |
| | made up to 10.00 ml with CHCl$_3$ | | |
| 1-Octene | | | |
| Amount | 2.020 g (18.0 mmol) | 3.211 g (18.0 mmol) | 1.000 g (7.68 mmol) |
| | made up to 10.00 ml with CHCl$_3$ | | |

Stock solution II: Metal complex or catalyst precursor

Catalyst type I: [MO$_5$(OER$_3$)]

M=Mo, W ; E=N, P ; R=$^n$Bu, $^n$Oct, $^n$Dodec, $^t$Bu

| Stock solution II | Amount |
|---|---|
| [MoO$_5$(OP$^n$Bu$_3$)] | 144 mg (0.365 mmol) |
| [MoO$_5$(OP$^n$Oct$_3$)] | 205 mg (0.365 mmol) |
| [MoO$_5$(OP$^n$Dodec$_3$)] | 234 mg (0.365 mmol) |
| [MoO$_5$(ON$^n$Bu$_3$)] | 138 mg (0.365 mmol) |
| [MoO$_5$(ON$^n$Oct$_3$)] | 199 mg (0.365 mmol) |
| [MoO$_5$(ON$^n$Dodec$_3$)] | 228 mg (0.365 mmol) |
| [MoO$_5$(OP$^t$Bu$_3$)] | 44 mg (0.365 mmol) |
| [WO$_5$(OP$^n$Oct$_3$)] | 237 mg (0.365 mmol) |
| [WO$_5$(ON$^n$Dodec$_3$)] | 293 mg (0.365 mmol) |
| [WO$_5$(OP$^t$Bu$_3$)] | 176 mg (0.365 mmol) |
| made up to 10.00 ml with CHCl$_3$ | |

Catalyst type II: [M(O)$_2$Cl$_2$dme] M=Mo, W

| Stock solution II | Amount |
|---|---|
| [MoO$_2$Cl$_2$dme] | 105 mg (0.365 mmol) |
| [WO$_2$Cl$_2$dme] | 137 mg (0.365 mmol) |
| in each case made up to 10.00 ml with CHCl$_3$ | |

Catalyst type III: [O$_3$ReR] R=Me, OSiMe$_3$

| Stock solution II | Amount |
|---|---|
| [O$_3$Re(OSiMe$_3$)] | 118 mg (0.365 mmol) |
| [O$_3$ReCH$_3$] | 91 mg (0.365 mmol) |
| [Re$_2$O$_7$.2 {ON$^n$Bu$_3$}] | 323 mg (0.365 mmol) |
| [Re$_2$O$_7$.2 {OP$^n$Bu$_3$}] | 336 mg (0.365 mmol) |
| in each case made up to 10.00 ml with CHCl$_3$ | |

Stock solution III: Ligand

[ONR$_3$] R=$^n$Bu, $^n$Dodec

[OPR$_3$] R=$^n$Bu, $^n$Oct, $^n$Dodec, $^t$Bu

[OASR$_3$] R=$^n$Dodec

| Stock solution III | Amount |
|---|---|
| [ON$^n$Bu$_3$] | 74 mg (0.365 mmol) |
| [ON$^n$Dodec$_3$] | 196 mg (0.365 mmol) |
| [OP$^n$Bu$_3$] | 80 mg (0.365 mmol) |
| [OP$^n$Oct$_3$] | 141 mg (0.365 mmol) |
| [OP$^n$Dodec$_3$] | 203 mg (0.365 mmol) |
| [OAs$^n$Dodec$_3$] | 219 mg (0.365 mmol) |
| made up to 10.00 ml with CHCl$_3$ | |

B Catalysis Procedure (general procedures)

Reactions using catalyst type I: [MO$_5$(OER$_3$)$_n$] (M=Mo, W; n=1,2)

4.0 mol % of catalyst

1000 μl of stock solution II (3.6×10$^{-2}$ mmol of [Mo] or [W], 4.0 mol %) and 500 μl of CHCl$_3$ are added to 500 μl of stock solution I (0.90 mmol of olefin/0.90 mmol of (TMS)$_2$O$_2$/0.38 mmol of $^n$Bu$_2$O=internal standard). The reaction mixture is stirred at 60° C. in an oil bath.

4.0 mol % of catalyst+1 eq. of [OER$_3$] (M:L=1:2) E=N, P; R=$^n$Bu, $^n$Oct, $^n$Dodec 1000 μl of stock solution II (3.6×10$^{-2}$ mmol of [Mo] or [W], 4.0 mol %) and 1000 μl of stock solution III (3.60×10$^{-2}$ mmol of [OER$_3$]) are added to 500 μl of stock solution I (0.90 mmol of olefin/0.90 mmol of (TMS)$_2$O$_2$/0.38 mmol of $^n$Bu$_2$O=internal standard). The reaction mixture is stirred at 60° C. in an oil bath.

0.1 mol % of catalyst

25 μl of stock solution II (0.9×10$^{-2}$ mmol of [Mo] or [W], 0.1 mol %) and 1000 μl of CHCl$_3$ are added to 500 μl of stock solution I (0.90 mmol of olefin/0.90 mmol of (TMS)$_2$O$_2$/0.38 mmol of $^n$Bu$_2$O=internal standard). The reaction mixture is stirred at 60° C. in an oil bath.

Reactions using catalyst type II: [M(O)$_2$Cl$_2$dme] (M=Mo, W)

4.0 mol % of catalyst without addition of ligand

1000 μl of stock solution II (3.60×10$^{-2}$ mmol of [Mo] or [W]) are added to 500 μl of stock solution I (0.90 mmol of olefin/0.90 mmol of (TMS)$_2$O$_2$/0.38 mmol of $^n$Bu$_2$O=internal standard). The reaction mixture is stirred at 60° C. in an oil bath.

4.0 mol % of catalyst+1 eq. of [OER$_3$] E=N, P, As; R=$^n$Bu, $^n$Oct, $^n$Dodec 1000 μl of stock solution II (3.6×10$^{-2}$ mmol of [Mo] or [W], 4.0 mol %) and 1000 μl of stock solution III (3.6×10$^{-2}$ mmol of [OER$_3$]) are added to 500 μl of stock solution I (0.90 mmol of olefin/0.90 mmol of (TMS)$_2$O$_2$/0.38 mmol of $^n$Bu$_2$O=internal standard). The reaction mixture is stirred at 60° C. in an oil bath.

4.0 mol % of catalyst+2 eq. of [OER$_3$] E=N, P, As; R=$^n$Bu, $^n$Oct, $^n$Dodec 1000 μl of stock solution II (3.6×10$^{-2}$ mmol of [Mo] or [W], 4.0 mol %) and 2000 μl of stock solution III (7.2×10$^{-2}$ mmol of [OER$_3$]) are added to 500 μl of stock solution I (0.90 mmol of olefin/0.90 mmol of (TMS)$_2$O$_2$/0.38 mmol of $^n$Bu$_2$O=internal standard). The reaction mixture is stirred at 60° C. in an oil bath.

2.0 mol % of catalyst+1 eq. of [OER$_3$] E=N, P, As; R=$^n$Bu, $^n$Oct, $^n$Dodec 500 μl of stock solution II (1.8×10⁻² mmol of [Mo] or [W], 2.0 mol %), 500 μl of stock solution III (1.80×10⁻² mmol of [OER₃]) and 500 μl of CHCl₃ are added to 500 μl of stock solution I (0.90 mmol of olefin/0.90 mmol of (TMS)₂O₂/0.38 mmol of "Bu₂O=internal standard). The reaction mixture is stirred at 60° C. in an oil bath.

2.0 mol % of catalyst+2 eq. of [OER₃] E=N, P, As; R="Bu, "Oct, "Dodec

500 μl of stock solution II (1.8×10⁻² mMol of [Mo] or [w], 2.0 mol %) and 1000 μl of stock solution III (3.60×10⁻² mmol of [OER₃]) are added to 500 μl of stock solution I (0.90 mmol of olefin/0.90 mmol of (TMS)₂O₂/0.38 mmol of "Bu₂O=internal standard). The reaction mixture is stirred at 60° C. in an oil bath.

0.1 mol % of catalyst+1 eq. of [OER₃] E=N, P, As; R="Bu, "Oct, "Dodec

25 μl of stock solution II (0.90×10⁻³ mmol of [Mo] or [W], 0.10 mol %), 25 μl of stock solution III (0.90×10⁻³ mmol of [OER₃]) and 500 μl of CHCl₃ are added to 500 μl stock solution I (0.90 mmol of olefin/0.90 mmol of (TMS)₂O₂/0.38 mmol of "Bu₂O=internal standard). The reaction mixture is stirred at 60° C. in an oil bath.

Reactions using catalyst type III: [O₃ReR] (R=Me, OSiMe₃)

0.01 mol % of catalyst+[OP("Dodec)₃]

2.5 μl of stock solution II (0.90×10⁻⁴ mmol of [Re], 0.01 mol %), 2.5 μl of stock solution III (0.90×10⁻⁴ mmol of [OP("Dodec)₃], 0.01 mol %) and 500 μl of CHCl₃ are added to 500 μl of stock solution I (0.90 mmol of olefin/0.90 mmol of (TMS)₂O₂/40 0.38 mmol of "Bu₂O). The reaction mixture is stirred at 60° C. in an oil bath.

0.1 mol % of catalyst+[OER₃] E=N, P, As; R="Bu, "Oct, "Dodec

25 μl of stock solution II (0.90×10⁻³ mmol of [Re], 0.10 mol %), 25 μl of stock solution III (0.90×10⁻³ mmol of [OER₃], 0.10 mol %) and 500 μl of CHCl₃ are added to 500 μl of stock solution I (0.90 mmol of olefin/0.90 mmol of (TMS)₂O₂/0.38 mmol of "Bu₂O). The reaction mixture is stirred at 60° C. in an oil bath.

0.1 mol % of catalyst without addition of ligand

25 μl of stock solution II (0.90×10⁻³ mmol of [Re], 0.10 mol %) and 500 Ml of CHCl₃ are added to 500 μl of stock solution I (0.90 mmol of olefin/0.90 mmol of (TMS)₂O₂/0.38 mmol of "Bu₂O). The reaction mixture is stirred at 60° C. in an oil bath.

1.00 mol % of catalyst without addition of ligand

250 μl of stock solution II (0.90×10⁻² mmol of [Re], 1.00 mol %) and 250 μl of CHCl₃ are added to 500 μl of stock solution I (0.90 mmol of olefin/0.90 mmol of (TMS)₂O₂/0.38 mmol of "Bu₂O). The reaction mixture is stirred at 60° C. in an oil bath.

4.0 mol % of catalyst without addition of ligand

1000 μl of stock solution II (3.6×10⁻² mmcl of [Re], 4.0 mol %) are added to 500 μl of stock solution I (0.90 mmol of olefin/0.90 mmol of (TMS)₂O₂/0.38 mmol of "Bu₂O). The reaction mixture is stirred at 60° C. in an oil bath.

C Results (Tabular)

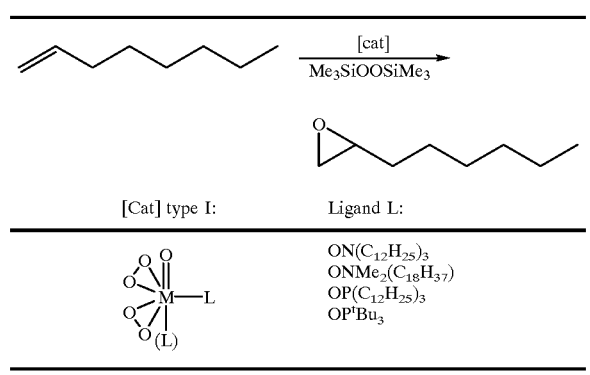

| Catalyst type I | [Cat] conc. [mol %] | Temperature [° C.] | Time [h] | Conversion [%] | Selectivity [%] |
|---|---|---|---|---|---|
| [Mo] · ONMe₂(C₁₈H₃₇) | 4 | 60 | 16 | 83 | 90 |
| [Mo] · ON(C₁₂H₂₅)₃ | 4 | 60 | 24 | 100 | >95 |
| [Mo] · OP(C₁₂H₂₅)₃ | 4 | 60 | 24 | 81 | 93 |
| [Mo] · 2 OP(C₁₂H₂₅)₃ | 4 | 60 | 24 | 100 | 93 |
| [Mo] · 2 ON(C₁₂H₂₅)₃ | 4 | 60 | 24 | 45 | 95 |
| [W] · ON(C₁₂H₂₅)₃ | 4 | 60 | 23 | 100 | 90 |
| [W] · OP(C₁₂H₂₅)₃ | 4 | 60 | 23 | 100 | 92 |
| [W] · OPᵗBu₃ | 4 | 60 | 23 | 100 | 50 |
| [Mo] · OPᵗBu₃ | 4 | 60 | 23 | 100 | 50 |

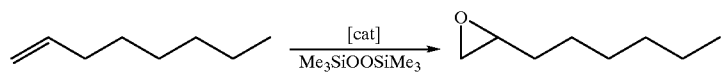

| [Cat] type II: | Ligand L: |
|---|---|
| 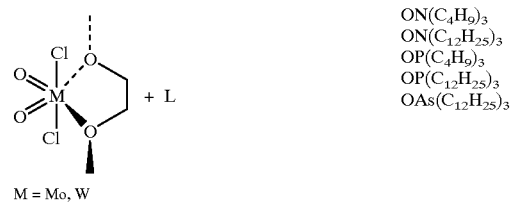 M = Mo, W  + L | ON(C$_4$H$_9$)$_3$<br>ON(C$_{12}$H$_{25}$)$_3$<br>OP(C$_4$H$_9$)$_3$<br>OP(C$_{12}$H$_{25}$)$_3$<br>OAs(C$_{12}$H$_{25}$)$_3$ |

| Catalyst type II | [Cat] conc. [mol %] | Temperature [° C.] | Time [h] | Conversion [%] | Selectivity [%] |
|---|---|---|---|---|---|
| [Mo] + ON(C$_4$H$_9$)$_3$ | 0.1 | 60 | 24 | 16 | 94 |
| [W] + ON(C$_4$H$_9$)$_3$ | 0.1 | 60 | 24 | 8 | >99 |
| [Mo] + OP(C$_4$H$_9$)$_3$ | 0.1 | 60 | 24 | 54 | 97 |
| [Mo] + ON(C$_4$H$_9$)$_3$ | 4 | 60 | 24 | 100 | >99 |
| [Mo] + OP(C$_4$H$_9$)$_3$ | 4 | 60 | 24 | 100 | 85 |
| [Mo] + ON(C$_{12}$H$_{25}$)$_3$ | 4 | 60 | 24 | 45 | >99 |
| [Mo] + OP(C$_{12}$H$_{25}$)$_3$ | 4 | 60 | 24 | 100 | 92 |
| [Mo] + 2 ON(C$_{12}$H$_{25}$)$_3$ | 4 | 60 | 24 | 100 | 99 |

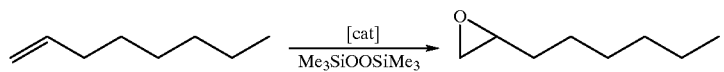

| [Cat] type III: | | Ligand L: |
|---|---|---|
| 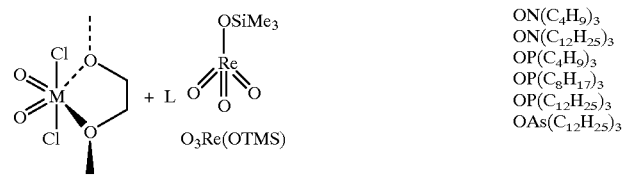 M = Mo, W  + L | O$_3$Re(OTMS) | ON(C$_4$H$_9$)$_3$<br>ON(C$_{12}$H$_{25}$)$_3$<br>OP(C$_4$H$_9$)$_3$<br>OP(C$_8$H$_{17}$)$_3$<br>OP(C$_{12}$H$_{25}$)$_3$<br>OAs(C$_{12}$H$_{25}$)$_3$ |

| Catalyst type III | [Cat] conc. [mol %] | Temperature [° C.] | Time [h] | Conversion [%] | Selectivity [%] |
|---|---|---|---|---|---|
| MTO without ligand | 0.1 | 60 | 6<br>24 | 13<br>98 | 98<br>98 |
| O$_3$Re(OTMS) without ligand | 0.1 | 60 | 6<br>24 | 14<br>100 | 90<br>99 |
| MTO + ON(C$_{12}$H$_{25}$)$_3$ | 0.1 | 60 | 6<br>24 | 21<br>98 | 92<br>98 |
| MTO + OP(C$_{12}$H$_{25}$)$_3$ | 0.1 | 60 | 6<br>24 | 70<br>99 | 99<br>99 |
| MTO + OAs(C$_{12}$H$_{25}$)$_3$ | 0.1 | 60 | 6<br>24 | 18<br>97 | 94<br>99 |
| O$_3$Re(OTMS) + ON(C$_{12}$H$_{25}$)$_3$ | 0.1 | 60 | 6<br>24 | 24<br>99 | 85<br>95 |
| O$_3$Re(OTMS) + OP(C$_{12}$H$_{25}$)$_3$ | 0.1 | 60 | 6<br>24 | 64<br>100 | 97<br>99 |
| O$_3$Re(OTMS) + OAs(C$_{12}$H$_{25}$)$_3$ | 0.1 | 60 | 6<br>24 | 19<br>90 | 95<br>99 |
| MTO + OP(C$_4$H$_9$)$_3$ | 0.1 | 60 | 6<br>24 | 75<br>100 | 99<br>99 |
| MTO + OP(C$_8$H$_{17}$)$_3$ | 0.1 | 60 | 6<br>24 | 76<br>100 | 99<br>99 |

-continued

| | [Cat] conc. [mol %] | Temperature [° C.] | Time [h] | Conversion [%] | Selectivity [%] |
|---|---|---|---|---|---|
| O$_3$Re(OTMS) + OP(C$_4$H$_9$)$_3$ | 0.1 | 60 | 6 | 65 | 99 |
| | | | 24 | 97 | 99 |
| O$_3$Re(OTMS) + OP(C$_8$H$_{17}$)$_3$ | 0.1 | 60 | 6 | 79 | 99 |
| | | | 24 | 98 | 98 |

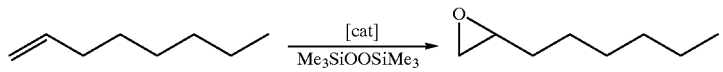

| [Cat] type IV: | Ligand L: |
|---|---|
| (structure) | ON(C$_4$H$_9$)$_3$ OP(C$_4$H$_9$)$_3$ |

| Catalyst type IV | [Cat] conc. [mol %] | Temperature [° C.] | Time [h] | Conversion [%] | Selectivity [%] |
|---|---|---|---|---|---|
| Re$_2$O$_7$ · 2 ON(C$_4$H$_9$)$_3$ | 0.1 | 60 | 3 | 14 | 95 |
| | | | 24 | 98 | 97 |
| Re$_2$O$_7$ · 2 OP(C$_4$H$_9$)$_3$ | 0.1 | 60 | 3 | 76 | 99 |
| | | | 24 | 99 | 99 |

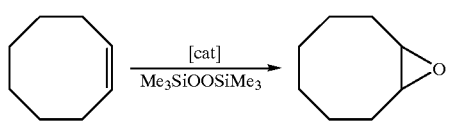

| [Cat] type II: | Ligand L: |
|---|---|
| (structure) M = Mo, W | ON(C$_{12}$H$_{25}$)$_3$ OP(C$_{12}$H$_{25}$)$_3$ |

| Catalyst type II | [Cat] conc. [mol %] | Temperature [° C.] | Time [h] | Conversion [%] | Selectivity [%] |
|---|---|---|---|---|---|
| [Mo] without ligand | 4 | 60 | 20 | 18 | >95 |
| [W] without ligand | 4 | 60 | 20 | 45 | >95 |
| [Mo] + ON(C$_{12}$H$_{25}$)$_3$ | 4 | 60 | 20 | 100 | >95 |
| [W] + ON(C$_{12}$H$_{25}$)$_3$ | 4 | 60 | 20 | 100 | >95 |

| [Cat] type I: | Ligand L: |
|---|---|
| (structure) M = Mo, W | ON(C$_8$H$_{17}$)$_3$ ON(C$_{12}$H$_{25}$)$_3$ ONMe$_2$(C$_{18}$H$_{37}$) OP(C$_8$H$_{17}$)$_3$ OP$^t$Bu$_3$ |

| Catalyst type I | [Cat] conc. [mol %] | Temperature [° C.] | Time [h] | Conversion [%] | Selectivity [%] |
|---|---|---|---|---|---|
| [Mo] · ON(C$_{12}$H$_{25}$)$_3$ | 4 | 25 | 50 | 97 | >95 |
| [W] · ON(C$_{12}$H$_{25}$)$_3$ | 4 | 25 | 50 | 27 | >95 |
| [M] · ON(C$_8$H$_{17}$)$_3$ | 4 | 60 | 20 | 97 | >95 |
| [Mo] · ON(C$_{12}$H$_{25}$)$_3$ | 4 | 60 | 20 | 97 | 95 |
| [Mo] · ONMe$_2$(C$_{18}$H$_{37}$) | 4 | 60 | 20 | 97 | >95 |
| [Mo] · OP(C$_8$H$_{17}$)$_3$ | 4 | 60 | 20 | 97 | >95 |
| [Mo] · OP$^t$Bu$_3$ | 4 | 60 | 20 | 78 | >95 |
| [Mo] · ONMe$_2$(C$_{18}$H$_{37}$) | 0.1 | 60 | 63 | 97 | >95 |
| [Mo] · ON(C$_{12}$H$_{25}$)$_3$ | 0.1 | 60 | 63 | 97 | >95 |

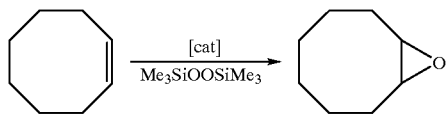

| -continued | | | | | |
|---|---|---|---|---|---|
| [Mo] + OP(C$_{12}$H$_{25}$)$_3$ | 4 | 60 | 23 | 100 | >95 |
| [W] + OP(C$_{12}$H$_{25}$)$_3$ | 4 | 60 | 23 | 100 | >95 |

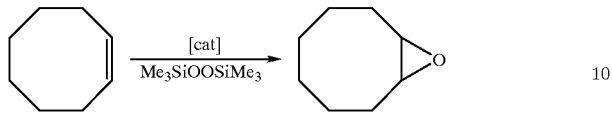

| [Cat] type III: | | Ligand L: |
|---|---|---|
| MTO | O$_3$Re(OTMS) | OP(C$_{12}$H$_{25}$)$_3$ |

| Catalyst type III | [Cat] conc. [mol %] | Temperature [° C.] | Time [h] | Conversion [%] | Selectivity [%] |
|---|---|---|---|---|---|
| MTO | 4 | 60 | 1 | 96 | >95 |
| O$_3$Re(OTMS) | 4 | 60 | 1 | 96 | >95 |
| MTO | 0.1 | 60 | 23 | 97 | >99 |
| O$_3$Re(OTMS) | 0.1 | 60 | 23 | 97 | >99 |
| O$_3$Re(OTMS) + OP(C$_{12}$H$_{25}$)$_3$ | 0.01 | 60 | 80 | 97 | 90 |

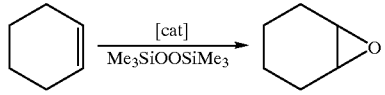

| [Cat] type II: | Ligand L: |
|---|---|
| M = Mo, W | OP(C$_4$H$_9$)$_3$ ON(C$_4$H$_9$)$_3$ |

| Catalyst type II: | [Cat] conc. [mol *] | Temperature [° C.] | Time [h] | Conversion [%] | Selectivity [%] |
|---|---|---|---|---|---|
| [Mo] + ON(C$_4$H$_9$)$_3$ | 2.0 | 40 | 6 | 21 | 90–99 |
| [Mo] + OP(C$_4$H$_9$)$_3$ | 2.0 | 40 | 6 | 54 | 90–99 |
| [W] + ON(C$_4$H$_9$)$_3$ | 2.0 | 40 | 6 | 25 | 90–99 |
| [W] + OP(C$_4$H$_9$)$_3$ | 2.0 | 40 | 6 | 44 | 90–99 |
| [Mo] + 2 ON(C$_4$H$_9$)$_3$ | 2.0 | 40 | 24 | 85 | 90–99 |
| [Mo] + 2 OP(C$_4$H$_9$)$_3$ | 2.0 | 40 | 24 | 77 | 90–99 |
| [W] + 2 ON(C$_4$H$_9$)$_3$ | 2.0 | 40 | 24 | 46 | 90–99 |
| [W] + 2 OP(C$_4$H$_9$)$_3$ | 2.0 | 40 | 24 | 100 | 90–99 |

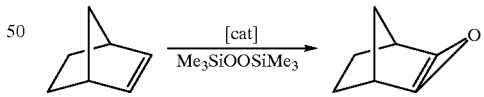

| [Cat] type II: | Ligand L: |
|---|---|
| M = Mo, W | OP(C$_{12}$H$_{25}$)$_3$ |

| | [Cat] conc. | Temperature | Time | Conversion | Selectivity |
|---|---|---|---|---|---|

-continued

| Catalyst type II: | [mol %] | [° C.] | [h] | [%] | [%] |
|---|---|---|---|---|---|
| [Mo] + OP(C$_{12}$H$_{25}$)$_3$ | 0.1 | 60 | 19 | 40 | 94 |
| [W] + OP(C$_{12}$H$_{25}$)$_3$ | 0.1 | 60 | 19 | 31 | 90 |

| [Cat] type III: | | Ligand L: |
|---|---|---|
| CH$_3$–Re(=O)$_3$ | OSiMe$_3$–Re(=O)$_3$ | OP(C$_{12}$H$_{25}$)$_3$ |
| MTO | O$_3$Re(OTMS) | |

| Catalyst type II: | [Cat] conc. [mol %] | Temperature [° C.] | Time [h] | Conversion [%] | Selectivity [%] |
|---|---|---|---|---|---|
| MTO + OP(C$_{12}$H$_{25}$)$_3$ | 0.1 | 60 | 19 | 100 | 86 |
| O$_3$Re(OTMS) + OP(C$_{12}$H$_{25}$)$_3$ | 0.1 | 60 | 19 | 90 | 91 |

Synthesis of Catalyst Complexes of the Type I

[M(O)(η$^2$-O$_2$)$_2$L] and [M(O)(η$^2$-O$_2$)$_2$L$_2$] (M=Mo, W)

To prepare complexes of the type [M(O)(η$^2$-O$_2$)L] (M=Mo, W; L=OP("Oct)$_3$, OP("Dodec)$_3$; ON("Oct)$_3$, ON("Dodec)$_3$, ONMe$_2$(stearyl), the respective ligand L is added to an aqueous stock solution of [M(O)(η$^2$-O$_2$)$_2$(H$_2$O$_2$)] (M=Mo, W).

A: Preparation of an Aqueous Stock Solution of

[M(O)(η$^2$-O$_2$)$_2$(H$_2$O$_2$)]

6.00 g (41.7 mmol) of [MoO$_3$] are suspended in 24.0 g (212 mmol) of 30% strength H$_2$O$_2$ solution with vigorous stirring. The colorless suspension is stirred at 40° C. for 4 hours, forming a clear, pale yellow solution which is stored at 4° C.

[M(O)(η$^2$-O$_2$)$_2$(H$_2$O$_2$)] content of stock solution A: 1.39 mmol/g.

B: Preparation of an Aqueous Stock Solution of

[W(O) (η$^2$-O$_2$)$_2$(H$_2$O$_2$)]

8.00 g (32.0 mmol) of [WO3·H$_2$O] are suspended in 24.0 g (212 mmol) of 30% strength H$_2$O$_2$ solution with vigorous stirring. The yellow suspension is stirred at 40° C. for 6 hours, forming a milky solution. After removing the insoluble residue (25 mg) by centrifugation, the clear, colorless solution is stored at 4° C.

[W(O)($^2$-O$_2$)$_2$(H$_2$O$_2$)] content of stock solution B: 1.01 mmol/g.

Preparation of [M(O)(η$^2$-O$_2$)$_2${ON"Oct)$_3$}]

570 mg (1.61 mmol) of [N("Oct)$_3$] are added dropwise at 10° C. to 1.50 g (2.15 mmol) of stock solution A while stirring, with a dark yellow oily phase being precipitated initially. After stirring vigorously for 8 hours at 25° C., a pale yellow precipitate forms. This is filtered off, washed with water (3 times with 5 ml each time) and dried at 25° C./10$^{-5}$ mbar for 6 hours.

Yield: 817 mg (93%) pale yellow, amorphous solid; DTA: 60° C. (exothermic decomposition); $^1$H-NMR (200.1 MHz, CDCl$_3$): δ=0.84 (t, 9 H, "Oct-(CH$_3$)-(8), 2J$_{HH}$=6.2 Hz), 1.10–1.45 (m, 30 H, "Oct-(CH$_2$)-(3–7)), 1.60–1.85 (m, 6 H, "Oct-(CH$_2$)-(2)), 3.31–3.51 (m, 6 H, "Oct-(CH$_2$)-(1)). $^{13}$C-NMR (50.1 MHz, CDCl$_3$): δ=14.02 ("Oct-C(8)), 22.55, 22.74, 26.09, 28.97, 29.13, 29.41 ("Oct-C(3–7)), 31.63 ("Oct-C(2)), 64.04 ("Oct-C(1)). IR (Nujol): ν=1722 w, 1096 m, 1320 w, 970 vs ν(Mo=O), 911 m, 851 vs ν(O—O), 820 w, 768 m, 724 m, 642 vs, 593 vs ν$_{as}$(Mo-($^2$-O$_2$)), 541 s ν$_s$(Mo-($^2$-O$_2$)), 519 m cm$^{-1}$. C$_{24}$H$_{51}$MoNO$_6$ (545.6) calc. C52.83; H9.42; N2.57; found C52.52; H9.50; N2.53.

Preparation of [Mo(O)(η$^2$-O$_2$)$_2${ON("Dodec)$_3$}]

A solution of 1.20 g (2.23 mmol) of [ON(dodec)$_3$] in 5 ml of CH$_2$Cl$_2$ are added at 25° C. to 2.00 g (2.87 mmol) of stock solution A while stirring. After stirring vigorously for 5 hours at 25° C., the organic phase is separated off, washed with water (3 times with 5 ml each time) and completely evaporated under reduced pressure. The pale yellow, amorphous residue is dried at 25° C./10$^{-5}$ mbar for 6 hours.

Yield: 2.81 g (95%) pale yellow, amorphous solid; DTA: 75° C. (exothermic decomposition); 1H-NMR (400.1 MHz, CDCl$_3$): δ=0.86 (t, 9 H, "Dodec-(CH$_2$)-(12), 2J$_{HH}$=7.2 Hz), 1.18–1.43 (m, 54 H, "Dodec-(CH$_2$)-(3–11)), 1.68–1.87 (m, 6 H, "Dodec-(CH$_2$)-(2)), 3.40–3.67 (m, 6 H, "Dodec-(CH$_2$)-(1)). 13C-NMR (100.6 MHz, CDCl$_3$): δ=14.04 ("Dodec-C(12)), 22.65, 26.22, 29.02, 29.22, 29.29, 29.35, 29.41, 29.49, 29.58 ("Dodec-C(3–11)), 31.87 ("Dodec-C(2)), 64.17 ("Dodec C(1)). IR (Nujol): C$_{36}$H$_{75}$MoNO$_6$(713.9) calc. C60.57; H10.59; N1.96; found C60.62; H10.72; N1.95.

Preparation of [W(O)(η$^2$-O$_2$)$_2${ON("Dodec)$_3$}]

A solution of 1.30 g (2.42 mmol) of [ON("Dodec)$_3$] in 5 ml of CH$_2$Cl$_2$ is added at 25° C. to 3.00 g (3.03 mmol) of stock solution B while stirring. After stirring vigorously for 5 hours at 25° C., the organic phase is separated off, washed with water (3 times with 5 ml each time) and completely evaporated under reduced pressure. The colorless, sticky residue is dried at 25° C./10$^{-5}$ mbar for 6 hours.

Yield: 1.84 g (95%) colorless, sticky wax; DTA: 68° C. (exothermic decomposition); 1H-NMR (400.1 MHz, CDCl$_3$): δ=0.85 (t, 9 H, "Dodec-(CH$_2$)-(12), 2J$_{HH}$=7.2 Hz), 1.15–1.41 (m, 54 H, "Dodec-(CH$_2$)-(3–11)), 1.68–1.87 (m, 6 H, "Dodec-(CH$_2$)-(2)), 3.37–3.51 (m, 6 H, "Dodec-(CH$_2$)-(1)). 13C-NMR (100.6 MHz, CDCl$_3$): δ=14.02 ("Dodec-C(12)), 22.63, 26.86, 26.34, 29.32, 29.36, 29.42, 29.60, 29.62, 29.64 ("Dodec-C(3–11)), 31.88 ("Dodec-C(2)), 64.30 ("Dodec C(1)). IR (Nujol): ν=1655 m, 1571 m, 1262 w, 1078 s, 965 s ν(W=O), 881 vs ν(O—O), 827 s, 729 s, 676 w, 626 s, 561 s ν$_{as}$(W-($^2$-O$_2$)), 500 m ν$_s$(W-($^2$-O$_2$)), 446 m cm$^{-1}$. C$_{36}$H$_{75}$WNO$_6$ (801.8) calc. C, 53.93; H, 9.43; N, 1.75 found C, 53.88; H, 9.29; N, 1.67.

Preparation of [Mo(O)(η$^{22}$-O$_2$)$_2${ONMe$_2$(stearyl)}]

6.00 g (5.74 mnol) of [ONMe$_2$(stearyl)] (30% in water) are added at 25° C. to 5.00 g (6.95 mmol) of stock solution A while stirring, with a pale yellow precipitate being formed spontaneously. After stirring vigorously for 2 hours, the precipitate is filtered off, is washed with water (3 times with 50 ml each time) and dried at 25° C./10$^{-5}$ mbar for 6 hours.

Yield: 2.00 g (71%) pale yellow, amorphous solid; DTA: 78° C. (exothermic decomposition); 1H-NMR (400.1 MHz, CDCl$_3$): δ=0.86 (t, 3 H, stearyl-(CH$_3$), 2J$_{HH}$=6.4 Hz), 1.15–1.31 (m, 32 H, stearyl-(CH$_2$)-(3–17)), 1.66–1.85 (m, 2 H, stearyl-(CH$_2$)-(2)), 3.37–3.51 (br, 8 H, ON-(CH$_3$)$_2$ and stearyl-(CH$_2$)-(1)). 13C-NMR (100.6 MHz, CDCl$_3$):

δ=14.09 (stearyl-C(12)), 22.11, 22.69, 23.24, 26.30, 29.18, 29.35, 29.42, 29.39, 29.42, 29.45, 29.57, 29.60, 29.62, 29.65, 29.69, 29.77, 29.82 (stearyl-C(3–17)), 31.95 (stearyl-C(2)), 56.46 (br, stearyl-C(1), ON-($CH_3$)$_2$). IR (Nujol): ν=1521 m, 1262 w, 1095 w, 1019 w, 980 s ν(Mo=O), 859 vs ν(O—O), 802 m, 718 s, 645 s, 596 s ν$_{as}$(Mo-($^2$-$O_2$)), 545 m ν$_s$(Mo-($^2O_2$)), 536 m cm$^{-1}$. $C_{20}H_{43}MoNO_6$ (489.5) calc. C, 49.07; H, 8.85; N, 2.86; found C, 49.07; H, 8.88; N, 2.82.

Preparation of [Mo(O)(η$^2$-$O_2$)$_2${OP("Oct)$_3$}]

371 mg (2.58 mmol) of $MoO_3$ are suspended in 3.0 ml (27.6 mmol) of 30% strength $H_2O_2$ solution with vigorous stirring. The colorless suspension is stirred at 40° C. for 4 hours, forming a clear, pale yellow solution. After addition of 4 ml of THF, 500 mg (1.29 mmol) of [OP("Oct)$_3$] are added at 25° C. while stirring. After stirring vigorously for 2 hours, the yellow solution is evaporated to about 3 ml under reduced pressure, with a yellow oil separating out. The reaction mixture is extracted with $CH_2Cl_2$ (3 times with 5 ml each time). The combined extracts are evaporated completely under reduced pressure. The pale yellow, wax-like residue is washed with water (2 times with 2 ml each time) and dried at 25° C./10$^{-5}$ mbar for 6 hours.

Yield: 675 mg (93%) pale yellow wax; DTA: 81° C. (exothermic decomposition); 1H-NMR (200.1 MHz, $CDCl_3$): δ=0.85 (t, 9 H, "Oct-($CH_2$)-(8), 2J$_{HH}$=6.6 Hz), 1.12–1.50 (m, 30 H, "Oct-($CH_2$)-(3–7)), 1.51–79 (m, 6 H, "Oct-($CH_2$)-(2)), 2.04–2.18 (m, 6 H, "Oct-($CH_2$)-(1)). 13C-NMR (50.3 MHz, $CDCl_3$): δ=14.72 (s, "Oct-C(8)), 21.89 (d, "Oct-C(3), $^3J_{CP}$=3.7 Hz), 26.32 (d, "Oct-C(1), 1J$_{CP}$=62.9 Hz), 23.27, 29.55, 29.65, 32.38 (each s, "Oct-C(4–7)}$_3$), 31.47 (d, "Oct-C(2), $^2$Jcp=15.7 Hz). 31P-NMR (81.0 MHz, $CDCl_3$): δ=83.21 ppm; IR (Nujol): ν=1245 m, 1228 w, 1203 m, 1078 s ν(P=O), 969 vs ν(Mo=O), 868 vs ν(O—O), 718 s, 695 s, 609 w, 592 vs ν$_{as}$(Mo-($^2$-O2)), 551 m vs(Mo-($^2$-$O_2$)), 526 m, 509m, 454 w cm$^{-1}$. $C_{24}H_{51}PMoO_6$ (650.5) calc. C, 51.24; H, 9.14; found C, 51.68; H, 9.45.

Preparation of [Mo(O)(η$^2$-$O_2$)$_2${OP("Dodec)$_3$}$_2$]

371 mg (2.58 mmol) of $MoO_3$ are suspended in 3.0 ml (27.6 mmol) of 30% strength $H_2O_2$ solution with vigorous stirring. The colorless suspension is stirred at 40° C. for 4 hours, forming a clear, pale yellow solution. After addition of 4 ml of THF, 2.86 g (5.16 mmol) of [OP("Dodec)$_3$] are added at 25° C. while stirring. After stirring vigorously for 2 hours, the yellow solution is evaporated to about 3 ml under reduced pressure, with a yellow oil separating out. The reaction mixture is extracted with $CH_2Cl_2$ (3 times with 5 ml each time). The combined extracts are evaporated completely under reduced pressure. The pale yellow, wax-like residue is washed with water (twice with 2 ml each time) and dried at 25° C./10$^{-5}$ mbar for 6 hours.

Yield: 3.20 g (97%) pale yellow wax; DTA : 39° C. (melting point); 119° C. (exothermic decomposition); 1H-NMR (200.1 MHz, $C_6D_6$): δ=0.92 (t, 18 H, "Dodec-($CH_2$)-(12), 2J$_{HH}$=6.2 Hz), 1.20–1.45 (br, 120 H, "Dodec-($CH_2$)-(3–11)), 1.40–2.05 (br, 12 H, "Dodec-($CH_2$)-(1)). 13C-NMR (50.3 MHz, $C_6D_6$): δ=14.38 (s, "Dodec-C(12)), 21.95 (br, "Dodec-C(3), 26.25 (d, "Dodec C(1), 1J$_{CP}$=85.2 Hz), 23.14, 29.73, 29.61, 29.70, 30.11, 30.20, 30.22, 32.37 (each s, "Dodec C(4–11)}$_3$), 31.51 (d, "Dodec C(2), 2J$_{CP}$=14.8 Hz). 31P-NMR (81.0 MHz, $C_6D_6$): δ=77.4 (OP$_{eq}$("Dodec)3), 57.4; (OP$_{ax}$("Dodec)$_3$)ppm; IR (Nujol): ν=1295 m, 1259 m, 1133 m, 1085 s ν(P=O), 952 vs ν(Mo=O), 872 s, 861 vs ν(O—O), 797 s, 716 m, 651 m, 579 s ν$_{as}$(Mo-($^2$-$O_2$)), 555 w ν$_s$(Mo-($^2$-$O_2$)) cm$^{-1}$. $C_{72}H_{150}P_2MoO_7$(1285.9) calc. C, 67.25; H, 11.76; found C, 67.13; H, 11.23.

Synthesis of catalyst complexes of type II

[M(O)$_2$Cl$_2$L$_2$] (M=Mo,W; L=ONR$_3$)

Preparation of [Mo(O)$_2$Cl$_2${ON("Dodec)$_3$}$_2$]

1.00 g (3.46 mmol) of [Mo(O)$_2$Cl$_2$(dme)] is suspended in 15 ml of hexane. At 25° C., 3.73 g (6.93 mmol) of [ON("Dodec)$_3$] are added to the colorless suspension with vigorous stirring, a yellow solution being formed over a period of 10 minutes. After stirring for 2 hours at 25° C., the solvent is evaporated under reduced pressure. The yellow, wax-like residue is freed of volatile constituents at 25° C./10$^{-5}$ mbar for 6 hours.

Yield: 4.30 g (98%) yellow, wax-like solid; Melting point: 32° C.; 1H-NMR (400.1 MHz, $CDCl_3$): δ=0.82 (t, 18 H, "Dodec-($CH_2$)-(12), 2J$_{HH}$=6.40 Hz), 1.12–1.33 (m, 108 H, "Dodec-($CH_2$)-(3–11)), 1.65–1.75 (m, 12 H, "Dodec-($CH_2$)-(2)), 3.52–3.56 (m, 12 H, "Dodec-($CH_2$)-(1)). 13C-NMR (100.6 MHz, $CDCl_3$): δ=13.97 ("Dodec-C(12)), 22.39, 26.18, 28.93, 28.97, 29.11, 29.23, 29.30, 29.41, 29.52 (nDodec-C(3–11)), 31.81 (nDodec-C(2)), 63.84 (nDodec C(1)). IR (Nujol): ν=2686 m und 2450 s ν(N—C—H), 1720 m ν(Mo—O—N), 1086 m ν(N—O), 952 vs ν$_s$(Mo=O), 910 vs ν$_{as}$(Mo=O), 868 m, 802 vs, 718 s, 659 w, 601 w, 551 w cm$^{-1}$. $C_{72}H_{150}Cl_2MoN_2O_4$(1274.8) calc. C, 67.84; H, 11.86; N, 2.20; found C, 67.63; H, 12.07; N, 2.12.

Preparation of [W(O)$_2$Cl$_2${ON("Dodec)$_3$}$_2$]

1.00 g (2.65 mmol) of [W(O)$_2$Cl$_2$(dme)] is suspended in 15 ml of hexane. At 25° C., 2.85 g (5.30 mmol) of [ON(dodec)$_3$] are added to the colorless suspension with vigorous stirring, a slightly yellow, clear solution being formed after 10 minutes. After stirring for 2 hours at 25° C., the solvent is evaporated under reduced pressure. The pale yellow, oily residue is freed of volatile constituents at 25° C./10$^{-5}$ mbar for 6 hours.

Yield: 3.54 g (98%) pale yellow oil; Melting point: 28° C.; 1H-NMR (400.1 MHz, $CDCl_3$): δ=0.81 (t, 18 H, "Dodec-($CH_2$)-(12), 2J$_{HH}$=6.80 Hz), 1.15–1.31 (m, 108 H, "Dodec-($CH_2$)-(3–11)), 1.65–1.75 (m, 12 H, "Dodec-($CH_2$)-(2)), 3.51–3.56 (m, 12 H, "Dodec-($CH_2$)-(1)). 13C-NMR (100.6 MHz, $CDCl_3$): δ=13.94 ("Dodec-C(12)), 22.54, 15 26.15, 28.94, 29.09, 29.20, 29.27, 29.39, 29.49, 29.50 ("Dodec-C (3–11)), 31.77 ("Dodec-C(2)), 63.78 ("Dodec C(1)). IR (Nujol): ν=2665 m und 2393 s ν(N—C—H), 1571 w, 1081 m ν(N—O), 977 vs ν$_s$(W=O), 897 m ν$_{as}$(W=O), 818 vs, 718 vs, 594 m, 450 vs cm$^{-1}$. $C_{72}H_{150}Cl_2N_2O_4$w(1362.7) calc. C, 63.46; H, 11.09; N, 2.06; found C, 63.40; H, 11.13; N, 2.07.

Preparation of [MO(O)$_2$Cl$_2${ON("Bu)$_3$}$_2$]

200 mg (0.69 mmol) of [Mo(O)$_2$Cl$_2$(dme)] are dissolved in 5 ml of $CHCl_3$. At 25° C., 279 mg (1.38 mmol) of [ON("Bu)$_3$] dissolved in 2 ml of $CHCl_3$ are added dropwise to the colorless solution with vigorous stirring, a pale yellow, clear solution being formed spontaneously. After stirring for 3 hours at 25° C., the yellow reaction solution is evaporated to dryness under reduced pressure. The yellow, oily residue is washed with hexane (3 times with 1 ml each time) and freed of volatile constituents at 25° C./10$^{-5}$ mbar for 6 hours.

Yield: 397 mg (96%) yellow oil; 1H-NMR (200.1 MHz, $CDCl_3$): δ=0.94 (t, 18 H, "Bu-($CH_3$)-(4), 2J$_{HH}$=7.20 Hz), 1.39 (sex, 12 H, "Bu-($CH_2$)-(3), 2J$_{HH}$=7.40 Hz), 1.66–1.82 (m, 12 H, "Bu-($CH_2$)-(2)), 3.55–3.63 (m, 12 H, "BU-($CH_2$)-(1)). 13C-NMR (50.1 MHz, $CDCl_3$): δ=13.59 ("Bu-C(4)), 19.49 ("-BuC(3)), 24.39 ("Bu-C(2)), 63.62 ("Bu -C(1)). IR (film): ν=2960 vs and 2869 vs ν(C—H), 2729 s and 2432 s ν(N—C—H), 1772 s ν(Mo—O—N), 1467 vs, 1381 s, 1261, 1164 m, 1061 w, 1031 m, 983 w, 954 vs $\nu_s$(Mo=O), 909 m $\nu_s$(N—O), 900 s $\nu_{as}$(MO=O), 795 vs, 735 m, 690 m, 432 m cm$^{-1}$. $C_{24}H_{54}Cl_2MoN_2O_4$ (601.6) calc. C, 47.92; H, 9.05; N, 4.66; found C, H, N.

Preparation of [W(O)$_2$Cl$_2$\{ON("Bu)$_3$\}$_2$]

250 mg (0.66 mmol) of [W(O)$_2$Cl$_2$(dme)] are dissolved in 5 ml of CHCl$_3$. At 25° C., 267 mg (1.33 mmol) of [ON ("Bu)$_3$] dissolved in 2 ml of CHCl$_3$ are added dropwise to the colorless solution with vigorous stirring. After stirring for 3 hours at 25° C., the colorless reaction solution is evaporated to dryness under reduced pressure. The colorless, oily residue is washed with pentane (3 times with 1 ml each time) and freed of volatile constituents at 25° C./10$^{-5}$ mbar for 6 hours, with a wax-like solid crystallizing after 3 hours.

Yield: 441 mg (97%) wax-like solid; 1H-NMR (200.1 MHz, CDCl$_3$): δ=0.95 (t, 18 H, "Bu-(CH$_3$)-(4), 2J$_{HH}$=7.3 Hz), 1.40 (sex, 12 H, "Bu-(CH$_2$)-(3), 2J$_{HH}$=7.4 Hz), 1.66–1.81 (m, 12 H, "Bu-(CH$_2$)-(2)), 1.56–3.64 (m, 12 H, "Bu-(CH$_2$)-(1)). 13C-NMR (50.1 MHz, CDCl$_3$): δ=13.62 ("Bu-C(4)), 19.52 ("Bu-C(3)), 24.41 ("Bu-C(2)), 63.33 ("Bu-C(1)). IR (film): ν=2954 vs and 2868 vs ν(C—H), 2720 s and 2428 s ν(N—C—H), 1772 m ν(W—O—N), 1467 s, 1431 s, 1386 s, 1332 m, 1317 m, 1260 m, 1165 m, 1119 m, 1063 m, 1032 m, 976 vs $\nu_s$(W=O), 895 m $\nu_{as}$(W=O), 906 s ν(N—O), 812 vs, 777 m, 585 m, 443 m cm$^{-1}$. $C_{24}H_{54}Cl_2WN_2O_4$(689.5) calc. C, 41.81; H, 7.89; N, 4.06; found C, H, N.

Catalyst Type II (Active Species):

[M(O)(η$^2$-O$_2$)Cl$_2$L$_2$] (M=Mo,W; L=ONR$_3$)

Preparation of [MO(O)(η$^2$-O$_2$)Cl$_2$\{ON("Dodec)$_3$\}$_2$]

At 0° C. 180 mg (1.01 mmol) of TMS$_2$O$_2$ are added dropwise to a pale yellow solution of 250 mg (0.87 mmol) of [Mo(O)$_2$Cl$_2$dme] and 931 mg (1.74 mmol) of ON("Dodec)$_3$\}$_2$ in 10 ml of CH$_2$Cl$_2$, with the reaction solution becoming intense yellow. Both monitoring of the reaction by GC and an analogous NMR test in CDCl$_3$ show the formation of (TMS)$_2$O from (TMS)$_2$O$_2$. After stirring for 2 hours at 25° C., the solvent is removed under reduced pressure. The orange crude product which remains is freed of volatile constituents at 25° C./10$^{-5}$ mbar for 6 hours.

Yield: 1170 mg (91%) orange oil; DTA : 31° C. (melting point), exothermic decomposition above 130° C.; 1H-NMR (200.1 MHz, CDCl$_3$): δ=0.84 (t, 18 H, "Dodec-(CH$_2$)-(12), 2J$_{HH}$=6.22 Hz), 1.13–1.40 (br, 108 H, "Dodec-(CH$_2$)-(3–11)), 1.65–1.80 (br, 12 H, "Dodec-(CH$_2$)-(2)), 3.45–3.62 (br, 12 H, "Dodec-(CH$_2$)-(1)). 13C-NMR (50.3 MHz, CDCl$_3$): δ=14.06 ("Dodec-C(12)), 22.52, 22.63, 26.13, 29.07, 29.30, 29.34, 29.45, 29.58, 29.59 ("Dodec-C(3–11)), 31.85 ("Dodec-C(2)), 64.23 ("Dodec C(1)). IR (film): ν=2997 vs, 2874 vs, 2696 s and 2393 s ν(N—C—H), 1730 s ν(N—O), 1463 vs, 1379 s, 1170 m ν(N—O), 952 vs $\nu_s$(Mo=O), 910 vs ν(O—O), 871 m, 793 vs, 718 s, 661 m, 601 m $\nu_s$(Mo-($^2$-O$_2$)), 559 m $\nu_{as}$(Mo-($^2$-O$_2$)) cm$^{-1}$. $_{72}$H$_{150}$Cl$_2$MoN$_2$O$_5$(1290.8) calc. C, 67.00; H, 11.71; N, 2.17; found C, 66.89; H, 11.36; N, 2.07.

Preparation of [W(O)(η$^2$-O$_2$)Cl$_2$\{ON("Dodec)$_3$\}$_2$]

At 0° C., 170 mg (0.95 mmol) of (TMS)$_2$O$_2$ are added to a solution of 300 mg (0.80 mmol) of [W(O)$_2$Cl$_2$dme] and 857 mg (1.60 mmol) of ON("Dodec)$_3$\}$_2$ in 10 ml of CH$_2$Cl$_2$. Both monitoring by GC and an analogous NMR test in CDCl$_3$ show the formation of (TMS)$_2$O from (TMS)$_2$O$_2$.

After stirring at 25° C. for 2 hours, the solvent is removed under reduced pressure. The colorless, wax-like residue is freed of volatile constituents at 25° C./10$^{-5}$ mbar for 6 hours.

Yield: 1010 mg (92%) colorless, wax-like solid; DTA : 38° C. (melting point), exothermic decomposition above 85° C.; 13C-NMR (50.3 MHz, CDCl$_3$): δ=13.97 ("Dodec-C (12)), 25.53, 25.55, 26.07, 29.10, 29.24, 29.25, 29.41, 29.50, 29.51 ("Dodec-C(3–11)), 31.77 ("Dodec-C(2)), 63.57 ("Dodec C(1)). IR (Nujol): ν=2665 m, 2393 s, 1730 m ν(W—O—N), 1563 m, 977 s ν(W=O), 865 s (O—O), 818 m, 718 s, 668 m, 609 m $\nu_{as}$(W-($^2$O$_2$)), 559 s $\nu_s$(W-(η$^2$-O$_2$)), 529 m cm$^{-1}$. $C_{72}H_{150}Cl_2WN_2O_5$(1378.7) calc. C, 62.73; H, 10.97; N, 2.02; found C, 61.07; H, 11.31; N, 1.90.

Synthesis of catalyst complexes of type IV

Preparation of [Re$_2$O$_7$\{ON("Bu)$_3$\}$_2$]

Variant A: [O$_3$Re(OTMS)] as starting material 187 mg (0.93 mmol) of ON"Bu$_3$ dissolved in 2 ml of CHCl$_3$ are added dropwise at 25° C. to a solution of 300 mg (0.93 mmol) of [O$_3$Re(OTMS)] in 5 ml of CHCl$_3$ with vigorous stirring. The reaction solution spontaneously becomes pale yellow. After stirring at 25° C. for 2 hours, the solvent is evaporated under reduced pressure, with the solution becoming colorless.

Monitoring of an analogous reaction carried out in CDCl$_3$ shows a decrease in the TMS signal on evaporation of the solvent.

The colorless, oily residue is freed of volatile constituents at 25° C./10$^{-5}$ mbar for 6 hours, leaving a colorless, wax-like solid.

Yield: 355 mg (86%) colorless, wax-like solid; Variant B: [Re$_2$O$_7$] as starting material; 202 mg (1.00 mmol) of ON"Bu$_3$ dissolved in 2 ml of CHCl$_3$ are added dropwise at 25° C. to a suspension of 243 mg (0.50 mmol) of [Re$_2$O$_7$] in 3 ml of CHCl$_3$, with a colorless clear solution being formed over a period of 10 minutes. After stirring at 25° C. for 2 hours, the solvent is removed completely under reduced pressure. The colorless, oily residue is freed of volatile constituents at 25° C./10$^{-5}$ mbar for 6 hours, leaving a colorless, wax-like solid.

Yield: 390 mg (88%) colorless, wax-like solid; 1H-NMR (200.1 MHz, CDCl$_3$): δ=0.96 (t, 18 H, "Bu-(CH$_3$)-(4), 2J$_{HH}$=7.31 Hz), 1.40 (sex, 12 H, "Bu-(CH$_2$)-(3), 2J$_{HH}$=7.32 Hz), 1.65–1.81 (m, 12 H, "Bu-(CH$_2$)-(2)), 3.41–3.50 (m, 12 H, "Bu-(CH$_2$)-(1)). 13C-NMR (50.1 MHz, CDCl$_3$): δ=13.33 ("Bu-C(4)), 19.33 ("Bu-C(3)), 24.13 ("Bu-C(2)), 64.08 ("Bu-C(1)). IR (film): ν=3085 s, 2961 s, 1886 w, 1469 s, 1383 m, 1345 m, 1118 m, 1062 m, 1026 m, 965 vs, 922 vs, 735 s, 502 w cm$^{-1}$. $C_{24}H_{54}N_2O_9Re_2$(887.1) calc. C, 32.50; H, 6.14; N, 3.16; found C, H, N.

We claim:

1. A process for preparing epoxides of the formula

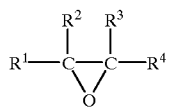

where R$^1$ to R$^4$ are identical or different and are hydrogen or substituted or unsubstituted alkyl, alkenyl, heteroalkyl, cycloalkyl, aryl or heteroaryl radicals, or the radicals R$^1$ to R$^4$ can also be linked to one another to form rings or are substituents based on elements of main groups IV to VII of the Periodic Table of the Elements, from olefins of the formula

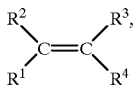

wherein bis(triorganosilyl) peroxides of the formula $$R^5R^6R^7Si\text{—}OO\text{—}SiR^5R^6R^7,$$

where $R^5$ to $R^7$ are hydrocarbon radicals which may be unsubstituted or substituted by functional groups, are used as epoxidizing agents in the presence of activators based on metallic acid derivatives of the formula $$[MO_XX_YL_Z]_n$$

where

M is a metal of transition groups IV to VII of the Periodic Table of the Elements, L are uncharged ligands selected from the group consisting of amine oxides, phosphine oxides, arsine oxides, stibine oxides, phosphoric triamides, formamides and pyridine N-oxides, X are anionic ligands selected from the group consisting of halides, alkyl groups, alkoxy groups, aryloxy groups, trialkylsilyl groups, hydroxyl groups, metallic anhydride groups of the formula —$OMO_x$, carboxylic ester groups, sulfonic ester groups, phosphonic ester groups, carbonic ester groups, sulfuric ester groups, phosphoric ester groups, hydroperoxy groups, peroxyalkyl groups and triorganosilylperoxy groups, where two variables X can also represent a peroxo function, x is an integer from 1 to 5, y is 0, 1 or 2, z is 1 or 2 and n is 1 or 2, where two uncharged ligands L, two anionic ligands X or one uncharged ligand L and one anionic ligand X may be linked to a chelating ligand either directly or via an alkylene bridge.

2. A process as claimed in claim 1, wherein the activators used are metallic acid derivatives in which M is molybdenum or tungsten and at the same time n is 1 or in which M is rhenium and n is 1 or 2.

3. A process as claimed in claim 1, wherein the activators used are metallic acid derivatives in which L are amine oxide or phosphine oxide ligands of the formulae

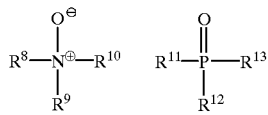

where $R^8$ to $R^{10}$ and $R^{11}$ to $R^{13}$ are identical or different $C_1$–$C_{30}$-alkyl, $C_7$–$C_{30}$-aralkyl or $C_6$–$C_{30}$-aryl or hetaryl radicals which may additionally contain ether oxygen atoms, carbonyl groups, hydroxyl groups, alkoxy groups, carboxyl groups, cyano groups, carboxylic ester groups, sulfo groups, phosphonic acid groups, nitro groups, halogen atoms and/or unsubstituted or $C_1$–$C_4$-alkyl-substituted amino groups as functional groups.

4. A process as claimed in claim 1, wherein the activators used are metallic acid derivatives in which, when is y=1 or 2, X is chloride, fluoride, $C_1$–$C_4$-alkyl, $C_1$–$C_4$-alkoxy, tri($C_1$–$C_4$-alkyl)silyl or metallic acid anhydride radicals of the formula —$OMoO_x$, —$OWO_x$ or —$OReO_x$.

5. A process as claimed in claim 1, wherein the epoxidizing agent used is bis(trimethylsilyl) peroxide.

6. A process as claimed in claim 1, wherein the olefin to be epoxidized is initially charged together with the bis(triorganosilyl) peroxides and, subsequently, the activator based based on metallic acid derivatives or a precursor thereof which is converted into the activator under the reaction conditions is added thereto.

7. A process as claimed in claim 1, wherein the epoxidation is carried out in an inert organic solvent at from 0 to 120° C.

8. A process as claimed in claim 1, wherein the activator based on metallic acid derivatives is used in bound form on an inorganic or organic support material which is insoluble in the reaction medium.

9. An activator complex for chemical reactions comprising from 0.1 to 50% by weight of one or more catalytically active metallic acid derivatives of the formula $$[MO_XX_YL_Z]_n$$

where

M is a metal of transition groups IV to VII of the Periodic Table of the Elements, L are uncharged ligands selected from the group consisting of amine oxides, phosphine oxides, arsine oxides, stibine oxides, phosphoric triamides, formamides and pyridine N-oxides, X are anionic ligands selected from the group consisting of halides, alkyl groups, alkoxy groups, aryloxy groups, trialkylsilyl groups, hydroxyl groups, metallic acid anhydride groups of the formula —$OMO_x$, carboxylic ester groups, sulfonic ester groups, phosphonic ester groups, carbonic ester groups, sulfuric ester groups, phosphoric ester groups, hydroperoxy groups, peroxyalkyl groups and triorganosilylperoxy groups, where two variables X can also represent a peroxo function, x is an integer from 1 to 5, y is 0, 1 or 2, z is 1 or 2 and n is 1 or 2, where two uncharged ligands L, two anionic ligands X or one uncharged ligand L and one anionic ligand X may be linked to a chelating ligand either directly or via an alkylene bridge, and from 50 to 99.9% by weight of one or more inorganic or organic support materials which are insoluble in the reaction medium and are selected from the group consisting of silicon dioxide, silica gels, silicas, aluminum oxides, kaolins, aluminum silicates, poly-tert-amine N-oxides, polyvinylpyridine N-oxides and hexamethylphosphoramide chemically fixed on a polystyrene matrix.

* * * * *